US009642700B2

(12) United States Patent
Sundler et al.

(10) Patent No.: US 9,642,700 B2
(45) Date of Patent: May 9, 2017

(54) PROSTHETIC HEART VALVE HAVING A POLYMERIC STENT

(75) Inventors: Sara Sundler, Uppsala (SE); Andreas Temnell, Uppsala (SE); Niklas Borg, Uppsala (SE); Anna Norlin Weissenrieder, Lidingö (SE)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 498 days.

(21) Appl. No.: 13/485,453

(22) Filed: May 31, 2012

(65) Prior Publication Data

US 2013/0325116 A1 Dec. 5, 2013

(51) Int. Cl.
*A61F 2/82* (2013.01)
*A61F 2/24* (2006.01)

(52) U.S. Cl.
CPC .............. *A61F 2/24* (2013.01); *A61F 2/2409* (2013.01); *A61F 2/2415* (2013.01); *A61F 2/2418* (2013.01); *A61F 2220/0008* (2013.01); *A61F 2220/0075* (2013.01)

(58) Field of Classification Search
CPC ................................. A61F 2/2418; A61F 2/82
USPC ................................................. 623/1.15, 1.26
See application file for complete search history.

(56) References Cited

U.S. PATENT DOCUMENTS

| 5,037,434 A * | 8/1991 | Lane ................. A61F 2/2418 623/2.18 |
| 6,610,088 B1 | 8/2003 | Gabbay |
| 2003/0171805 A1 | 9/2003 | Berg et al. |
| 2004/0220663 A1 * | 11/2004 | Rivelli, Jr. .................. 623/1.22 |
| 2006/0271167 A1 * | 11/2006 | Knight .......................... 623/1.26 |
| 2006/0276888 A1 | 12/2006 | Lee et al. |
| 2008/0147179 A1 | 6/2008 | Cai et al. |

FOREIGN PATENT DOCUMENTS

| WO | 2008079272 A2 | 7/2008 |
| WO | 2011058385 A1 | 5/2011 |

OTHER PUBLICATIONS

International Search Report and Written Opinion for Application No. PCT/US2013/042857 dated Sep. 19, 2013.

* cited by examiner

*Primary Examiner* — Matthew Schall
(74) *Attorney, Agent, or Firm* — Lerner, David, Littenberg, Krumholz & Mentlik, LLP (57) ABSTRACT

A prosthetic heart valve includes annularly spaced commissure portions, each of which includes a tip. The stent is formed from a polymeric material, and is specifically configured to perform similarly to conventional metal stents. A first fabric covers each of the tips, and a second fabric covers the first fabric and remaining exposed portions of the stent. A first layer of tissue covers the second fabric, and a second layer of tissue overlies the second fabric. The second layer of tissue includes leaflet portions that extend inwardly between annularly adjacent ones of the commissure portions.

12 Claims, 11 Drawing Sheets

PROSTHETIC HEART VALVE HAVING A POLYMERIC STENT

FIELD OF THE INVENTION

The present invention is related to prosthetic heart valve replacement, and more particularly to aortic valve replacement using a biological prosthetic heart valve that has a monolithic polymeric stent.

BACKGROUND OF THE INVENTION

The heart is the core muscle responsible for pumping life-sustaining blood through the body via an intricate network of vessels. It works ceaselessly and beats 100,000 times a day and 40 million times a year.

In its simplest form, the human heart can be described as a four-chamber structure, each chamber filling with a new round of blood with every beat. The chambers are called the right atrium, left atrium, right ventricle and left ventricle. Each chamber is connected with a valve. These valves operate similarly to check valves and ensure blood flows in the proper direction through the heart. The right chambers receive blood that is low in oxygen and then pump the blood through the pulmonary artery and into the lungs. The left side of the heart receives the now oxygen-rich blood from the lungs and the left ventricle pumps the blood out to the body, through the aorta.

When the valves of the human heart cease to work properly, leakage can occur between the chambers of the heart, resulting in a lower blood pressure or high resistance for the blood to pass through. One solution is to replace malfunctioning valves with either a mechanical or a biological valve.

A stented tissue heart valve is a replacement prosthetic heart valve composed of a stent covered in biological tissue. The stented tissue heart valve replaces the diseased, damaged or malfunctioning valve, such as the aortic valve between the left ventricle and the aorta. It is designed for supra-annular placement. Its functional purpose is to maintain structural integrity with a high-strength fatigue-resistant stent at the core.

Through cardiac surgery, the malfunctioning heart valve can be removed and then replaced by the stented tissue valve. Selection of the appropriate size replacement valve is of great importance. Prosthetic heart valves typically have a diameter between about 19 mm and about 29 mm. The valve size selection is determined through a sizer-replica of the 19-29 mm diameter valve. Once an appropriate size is selected to fit a patient, sutures are sewn into the aortic tissue. The sewing cuff of the prosthetic valve is then threaded over these sutures, and the valve is transferred down to the aortic opening where it is firmly attached.

Numerous replacement prosthetic heart valves have been designed. Conventional prosthetic heart valves are manufactured from a metallic stent assembly and bovine pericardium tissue. The stent assembly consists of a core (called a stent) formed from metal, such as titanium alloy, a polyester fabric forming the sewing cuff and porcine tissue covering all edges of the stent. The bovine pericardium tissue is attached to the stent assembly to form three leaflets which cooperate to permit blood to flow in one direction, but not the other.

Figure 1:
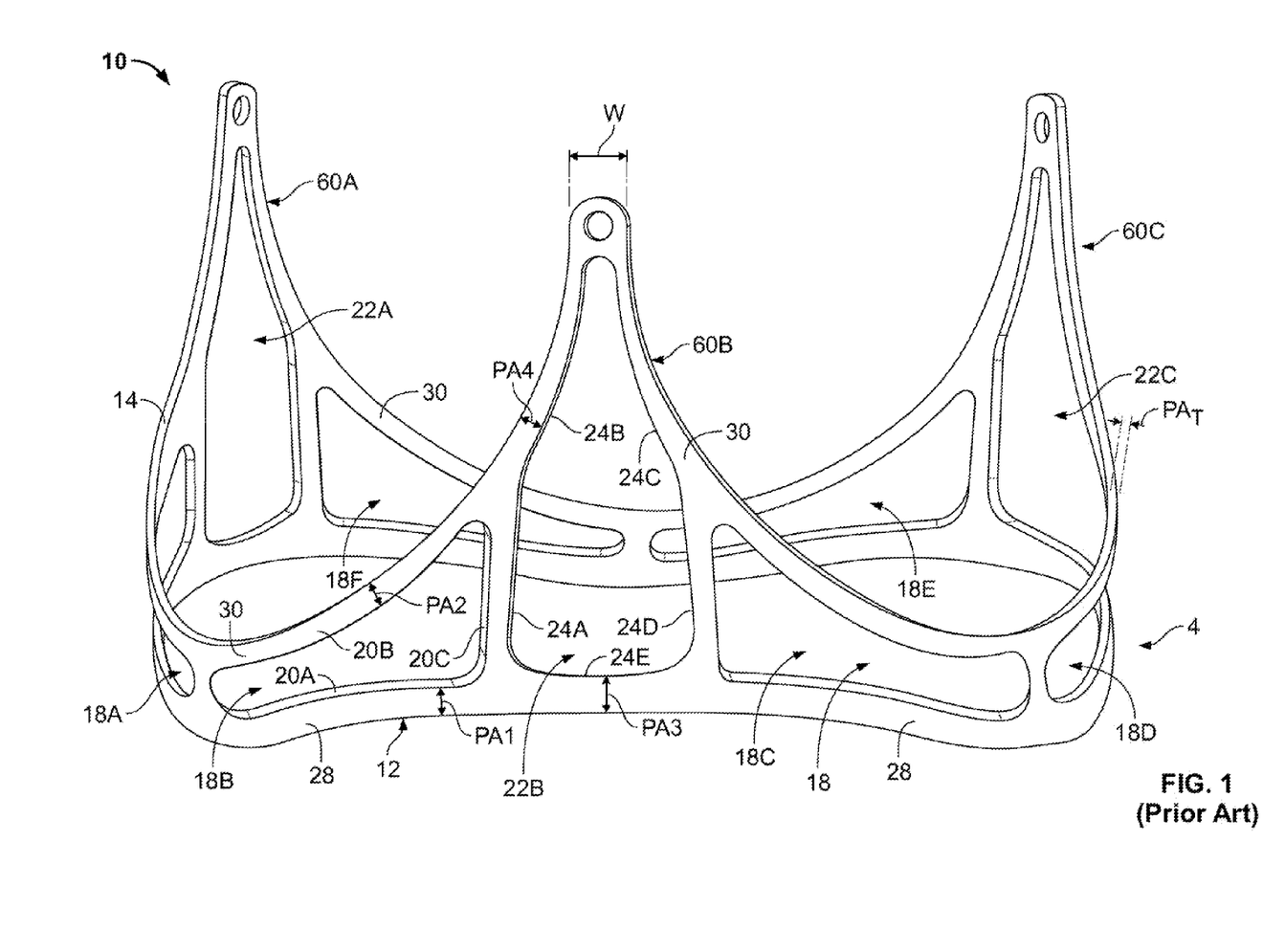
FIG. 1 is a perspective view of a stent of a prosthetic heart valve according to the prior art.

An example of a stent 10 for use in a conventional prosthetic heart valve is shown in FIG. 1, and is discussed more fully in U.S. Patent Application Publication No. 2008/0147179, the disclosure of which is hereby incorporated herein by reference. Stent 10 is an annular structure formed from metal, such as titanium. In a typical process, stent 10 may be formed by laser cutting a titanium tube to the desired shape, followed by electro-polishing the resultant structure. The stent structure includes a base 4, commissure posts 60A-60C extending from the base, a blood inflow edge 12, and a blood outflow edge 14. Stent 10 can have a diameter ranging from about 19 mm to about 29 mm and a wall thickness $PA_T$ ranging from about 0.25 mm to about 0.33 mm, depending on the selected size of the stent. The width W of each commissure post typically ranges from about 1.45 mm to about 1.51 mm.

Numerous geometrically-shaped openings are provided within metallic stent 10. Elongated openings 22A, 22B, and 22C extend along the lengths of posts 60A-60C. The portions of elongated openings 22 closer to inflow edge 12 are generally rectangular in shape, whereas the portions of elongated openings 22 closer to outflow edge 14 are more triangular in shape. Each elongated opening 22 includes five distinct edges 24A, 24B, 24C, 24D, and 24E that generally form the shape of an elongated bottle.

Openings 18A-18F extend around the circumference of base 4. Each opening 18 includes three distinct edges 20A, 20B, and 20C that generally form the shape of a right triangle, and more specifically a 30-60-90 right triangle. Edge 20C is directly adjacent an edge 24A or 24D of an opening 22 in a commissure post. As shown, openings 18, 22 are positioned a predetermined distance away from the inflow and outflow edges of stent 10. As a result, inflow edge portion 28 has a width PA1 between inflow edge 12 and edges 20A of openings 18, and a width PA3 between inflow edge 12 and edges 24E of openings 22. Similarly, outflow edge portion 30 has a width PA2 between outflow edge 14 and edges 20B of openings 18, and a width PA4 between outflow edge 14 and edges 24B, 24C of openings 22. The widths PA1 and PA3 of inflow edge portion 28 are substantially similar to the widths PA2 and PA4 of the outflow edge portion 30. Such dimensional uniformity in stent 10 is believed to provide a stable structure that can minimize deformation of the stent, especially during handling of the stent by surgeons.

Despite the improved design of the stent shown in FIG. 1, there is still room for further improvements. For example, because of the plastic behavior of metals, metallic stents are subject to deformation during handling and implantation in a patient. A need therefore exists for prosthetic valves having improved stent designs that are less prone to deformation, but that are capable of reliable production.

SUMMARY OF THE INVENTION

One aspect of the present invention provides prosthetic heart valves having an annular stent comprised of a polymeric material. In one embodiment of the heart valve, the stent may have a base and annularly spaced commissure portions projecting from the base, each commissure portion including a tip. The stent may have a wall thickness between about 0.50 mm and about 1.15 mm. The heart valve may further include a fabric covering the stent; a first layer of tissue covering the fabric; and a second layer of tissue overlying the first layer of tissue and including leaflet portions that extend inwardly between annularly adjacent ones of the commissure portions. The heart valve may further include a sewing cuff structure adjacent the base of the stent.

Preferably, the polymeric material is polyetheretherketone. Alternatively, the polymeric material may be selected from the group consisting of polysulfone, polyphenylsulfone, liquid crystal polymer, polyoxymethylene, and polypropylene.

At least one of the tips may have a tip deflection less than about 3 mm when the heart valve is in use in a patient. Preferably, the tip deflection is greater than about 0 mm and less than about 3 mm.

The stent may include an inflow edge adjacent the base, an outflow edge adjacent the tips, and a plurality of openings between the inflow edge and the outflow edge. Each opening may have a first edge at a first spaced distance from the inflow edge and a second opening at a second spaced distance from the outflow edge, the second spaced distance being greater than the first spaced distance. The first spaced distance may be between about 0.4 mm and 1.2 mm. The second spaced distance may be between about 0.6 mm and 2.2 mm.

The first layer of tissue of the prosthetic heart valve may comprise mammalian pericardium tissue, in particular porcine pericardium tissue. The second layer of tissue may also comprise mammalian pericardium tissue, in particular bovine pericardium tissue.

Another embodiment of the prosthetic heart valve includes an annular stent having annularly spaced commissure portions, each commissure portion including a tip. The stent may be comprised of a polymeric material having a thickness of between about 0.50 mm and about 1.15 mm. The heart valve may further include a first fabric covering each of the tips; a second fabric covering the first fabric and remaining exposed portions of the stent; a first layer of tissue covering the second fabric; and a second layer of tissue overlying the first layer of tissue and including leaflet portions that extend inwardly between annularly adjacent ones of the commissure portions.

At least one of the tips may have a tip deflection less than about 3 mm when the heart valve is in use in a patient. Preferably, the tip deflection is greater than about 0 mm and less than about 3 mm when the heart valve is in use in a patient.

The first layer of tissue of the prosthetic heart valve may comprise mammalian pericardium tissue, particularly porcine pericardium tissue. The second layer of tissue may also comprise mammalian pericardium tissue, particularly bovine pericardium tissue.

The stent may include a base, an inflow edge adjacent the base, an outflow edge adjacent the tips and a sewing cuff structure adjacent the inflow edge.

In yet another embodiment, the prosthetic heart valve may include an annular stent comprised of a polymeric material. The stent may have annularly spaced commissure portions, each commissure portion having a tip. The heart valve may further include a fabric covering the stent; a first tissue layer covering the fabric; and a second tissue layer overlying the first tissue layer and including leaflet portions that extend inwardly between annularly adjacent ones of the commissure portions.

Another aspect of the present invention provides a method of making a prosthetic heart valve. The method includes providing an annular stent comprised of a polymeric material. The stent has a base and annularly spaced commissure portions projecting from the base, each commissure portion including a tip. The method further includes covering the stent with a fabric; covering the fabric with a first layer of tissue; and arranging a second layer of tissue over the first layer of tissue, the second layer of tissue including leaflet portions that extend inwardly between annularly adjacent ones of the commissure portions. The step of providing the stent may include molding the polymeric material using an injection molding process.

In another method according to this aspect of the invention, a method of making a prosthetic heart valve includes providing an annular stent comprised of a polymeric material having a thickness between about 0.50 mm and about 1.15 mm. The stent has a base and annularly spaced commissure portions projecting from the base, each commissure portion including a tip. The method further includes covering each of the tips with a first fabric; covering the first fabric and remaining exposed portions of the stent with a second fabric; covering the second fabric with a first layer of tissue; and arranging a second layer of tissue over the first layer of tissue, the second layer of tissue including leaflet portions that extend inwardly between annularly adjacent ones of the commissure portions. The step of providing the stent may include molding the polymeric material using an injection molding process.

DETAILED DESCRIPTION

Figure 2:
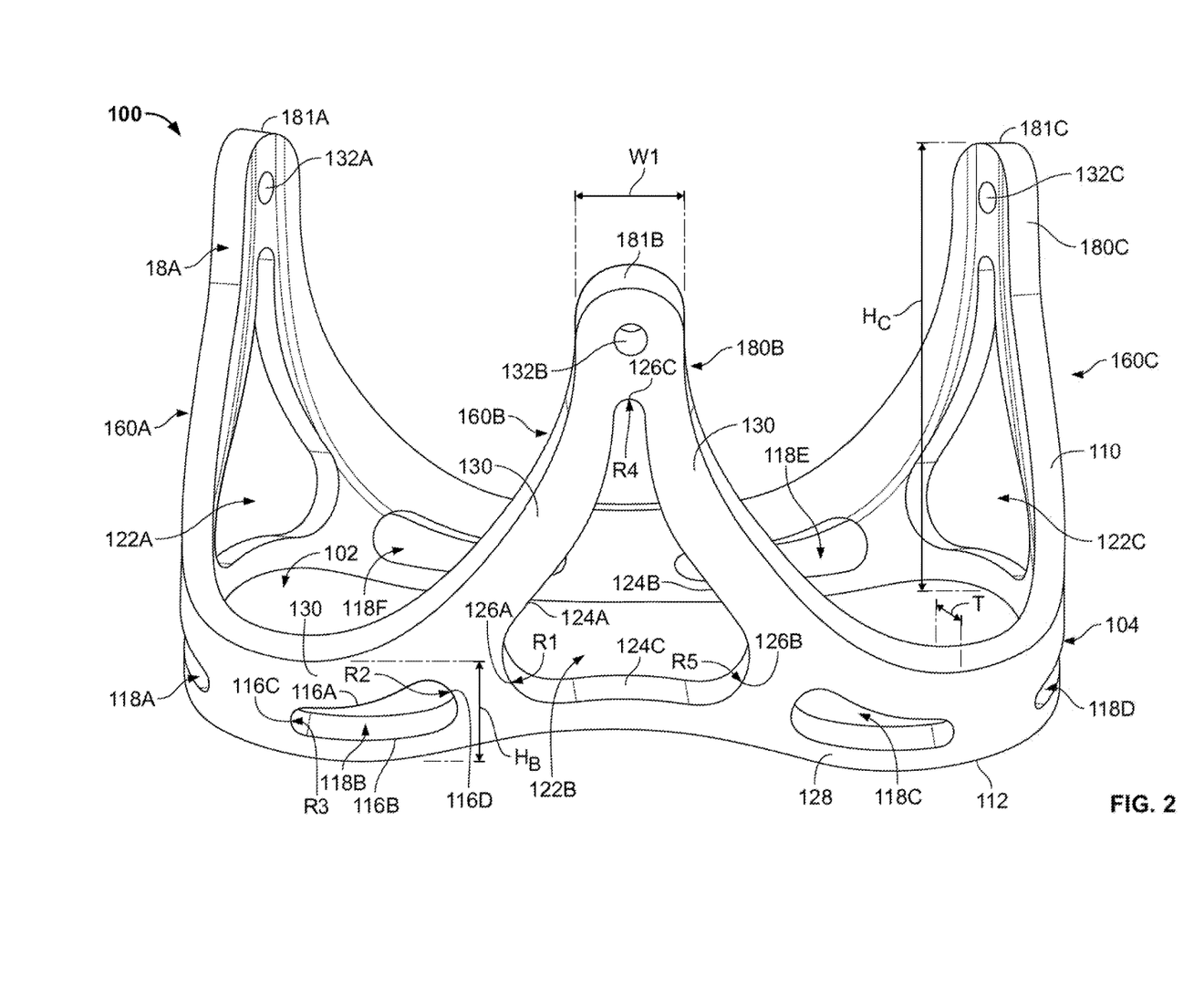
FIG. 2 is a perspective view of a stent of a prosthetic heart valve in accordance with one embodiment of the invention.

Referring now to FIG. 2, an illustrative embodiment of a stent 100 of a prosthetic heart valve (FIG. 14) in accordance with one embodiment of the invention is shown. Stent 100 is a hollow annular structure for use as a component of a tricuspid valve for aortic valve replacement. The outer diameter D (FIG. 3) of the valve stent may range from about 18 mm to about 24 mm, depending on the size of the native valve annulus into which the prosthetic valve is to be implanted. Stent 100 has a continuous and curved stent base 104 and three commissure posts 160A-160C that surround an annular opening 102. An inflow edge 112 and outflow edge 110 define the longitudinal ends of stent 100. Stent base 104 has a nonuniform height $H_B$ that extends from inflow edge 112 to the portions of outflow edge 110 that extend between commissure posts 160A, 160B and 160C.

The three commissure posts 160A, 160B and 160C may be evenly spaced around stent base 104. Commissure posts 160A-160C extend generally upwardly from base 104 to post tips 180A-180C positioned at the free ends of the respective commissure posts, with the commissure tips terminating at respective apexes 181A-181C that lie on the outflow edge 110. Each commissure post 160 may have a height $H_C$ that extends from the inflow edge 112 to a respective apex 181 and an overall triangular shape. The height $H_C$ may be between about 10.0 mm and about 15.0 mm, with the overall height of stent 100, taking into consideration the scalloped profile of inflow edge 112 (described below), being between about 11 mm and about 17 mm. The post tips 180A-180C each may have the same predetermined width W1, which preferably is greater than the width of conventional metal stents. The width W1 may range from about 2.0 mm to about 3.7 mm, depending on the selected size of stent 100.

Outflow edge 110 extends continuously along the outermost top portion of stent 100. As shown, outflow edge 110 extends between and around each commissure post 160. The contour of outflow edge 110 is scalloped, extending downwardly from the apex 181 of one post tip 180 and upwardly toward the apex of the next adjacent post tip. For example, outflow edge 110 extends downwardly from the apex 181B of post tip 180B towards base 104, and then upwardly along post tip 180C to the apex 181C thereof. The inflow edge 112 may also be slightly curved or scalloped. In that regard, inflow edge 112 may rise in the regions longitudinally below each commissure post 160A-160C and fall in the regions therebetween.

Geometric openings are provided within stent 100 in order to increase the flexibility of the stent and withstand fatigue, particularly as the valve leaflets open and close during use. Turning first to base 104, base openings 118A, 118B, 118C, 118D, 118E and 118F may extend around the base 104. Two of these base openings may be provided between each pair of adjacent commissure posts 160. For example, two base openings 118C,118D may be provided between commissure posts 160B and 160C. Each base opening 118 has a top edge 116A and a bottom edge 116B joined together by a first rounded end 116C farther from a commissure post and a second rounded end 116D closer to the commissure post. Bottom edge 116B may extend generally parallel to inflow edge 112, while top edge 116A extends generally parallel to outflow edge 110. Accordingly, edges 116A and 116B may diverge from one another as they approach each commissure post 160, with the second rounded end 116D having a larger radius of curvature R2 than the radius of curvature R3 of the first rounded end 116C. The radius of curvature R2 may be between about 0.4 mm and about 0.90 mm and the radius of curvature R3 may be between about 0.25 mm and about 0.50 mm. Geometric openings may also be present within each commissure post 160. Thus, commissure posts 160A-160C may have respective post openings 122A-122C that extend along the height $H_C$ of the commissure post. For example, post opening 122B may have a first rounded edge 124A, a second rounded edge 124B and a third rounded edge 124C which collectively are joined in a generally triangular shape. The first and second rounded edges 124A,124B may generally follow the contour of outflow edge 110, whereas the third rounded edge 124C may generally follow the contour of inflow edge 112. First rounded edge 124A and third rounded edge 124C join at a corner 126A having a radius of curvature R1 between about 0.70 mm and about 1.60 mm. Similarly, third rounded edge 124C and second rounded edge 124B join at a corner 126B having a radius of curvature R5 that is substantially the same as the radius of curvature R1, i.e., between about 0.70 mm and about 1.60 mm. Finally, first rounded edge 124A and second rounded edge 124B join at a corner 126C having a radius of curvature R4 between about 0.45 mm and about 0.60 mm. Additional round openings 132A-132C may be provided in respective post tips 180A-180C above post openings 122.

Figure 4:
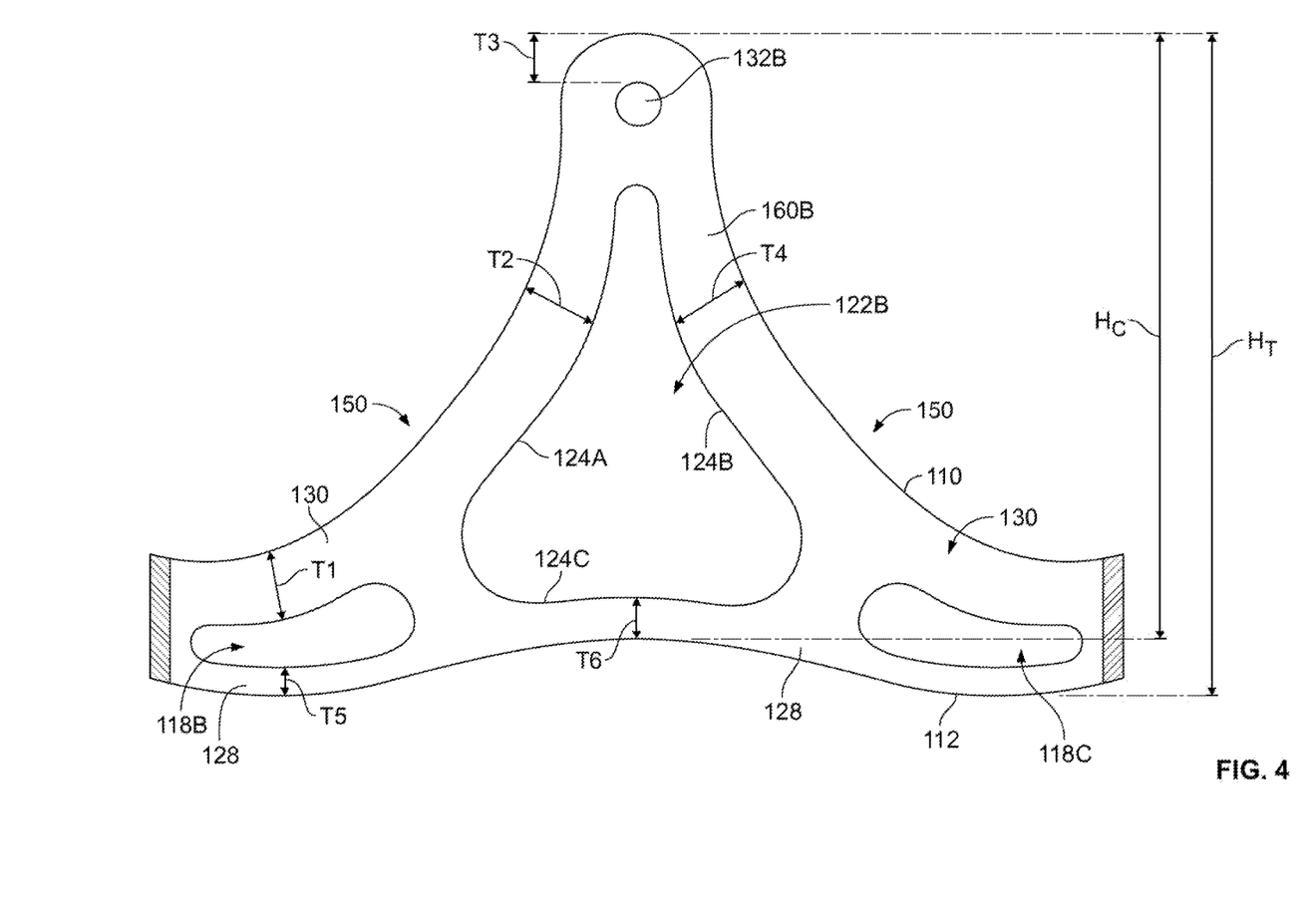
FIG. 4 is a ⅓ sectional front elevation of the stent shown in FIG. 2.

The geometry of stent 100 will be described in more detail with reference to FIG. 4. Base openings 118, post openings 122, and round openings 132 may be spaced a predefined distance away from outflow edge 110 and inflow edge 112. An inflow edge portion 128 and an outflow edge portion 130 are defined between the edges of the respective openings and the respective outflow and inflow edges 110,112. Outflow edge portion 130 has a width T1 between outflow edge 110 and edge 116A of base opening 118; widths T2 and T4 between respective edges 124A,124B of post opening 122 and outflow edge 110; and width T3 between opening 132 and post apex 181. Similarly, inflow edge portion 128 has a width T5 between edge 116B of base opening 118 and inflow edge 112; and a width T6 between edge 124C of post opening 122 and inflow edge 112. Generally, the width (T1-14) of outflow edge portion 130 is greater than the width (T5,T6) of inflow edge portion 128. More particularly, outflow edge portion 130 may have a width between about 0.6 mm and about 2.2 mm, whereas inflow edge portion 128 may have a width between about 0.4 mm and about 1.2 mm. It will be appreciated from FIG. 4 that widths T2 and T4 may not be constant along their entire lengths. That is, in order to have corner 126C as close as possible to the apex 181 of the commissure post 160, and to have a large enough radius R4 at the corner to minimize stresses thereat, the width of outflow edge portion 130 may taper downwardly as it approaches corner 126C. Similarly, the other widths, namely, T1, T3, T5 and T6, may not be constant along their entire lengths, but may vary slightly to accommodate the radii of openings 118 and 122.

Stent 100 is formed from a polymeric material, and may be formed from an injection molded monolithic polymer. As used herein, the term "monolithic" refers to a structure that is formed entirely from a polymeric material, rather than to structures that may have a non-polymeric core and a polymeric coating, or a polymeric core and a non-polymeric coating. The term "monolithic" is not intended to be limited to structures formed from a single polymeric material. Thus, "monolithic" polymer structures include those that may be formed from a mixture of different polymeric materials, as well as those that may include layers or regions formed from the same or different polymeric materials. Moreover, although injection molding is a preferred manufacturing method for stent 100, it is contemplated that the stent may be formed by other techniques known in the art. For example, stent 100 may be formed by laser cutting a tube of polymeric material in a manner similar to the manner in which the prior art metal stents are made.

Figure 5:
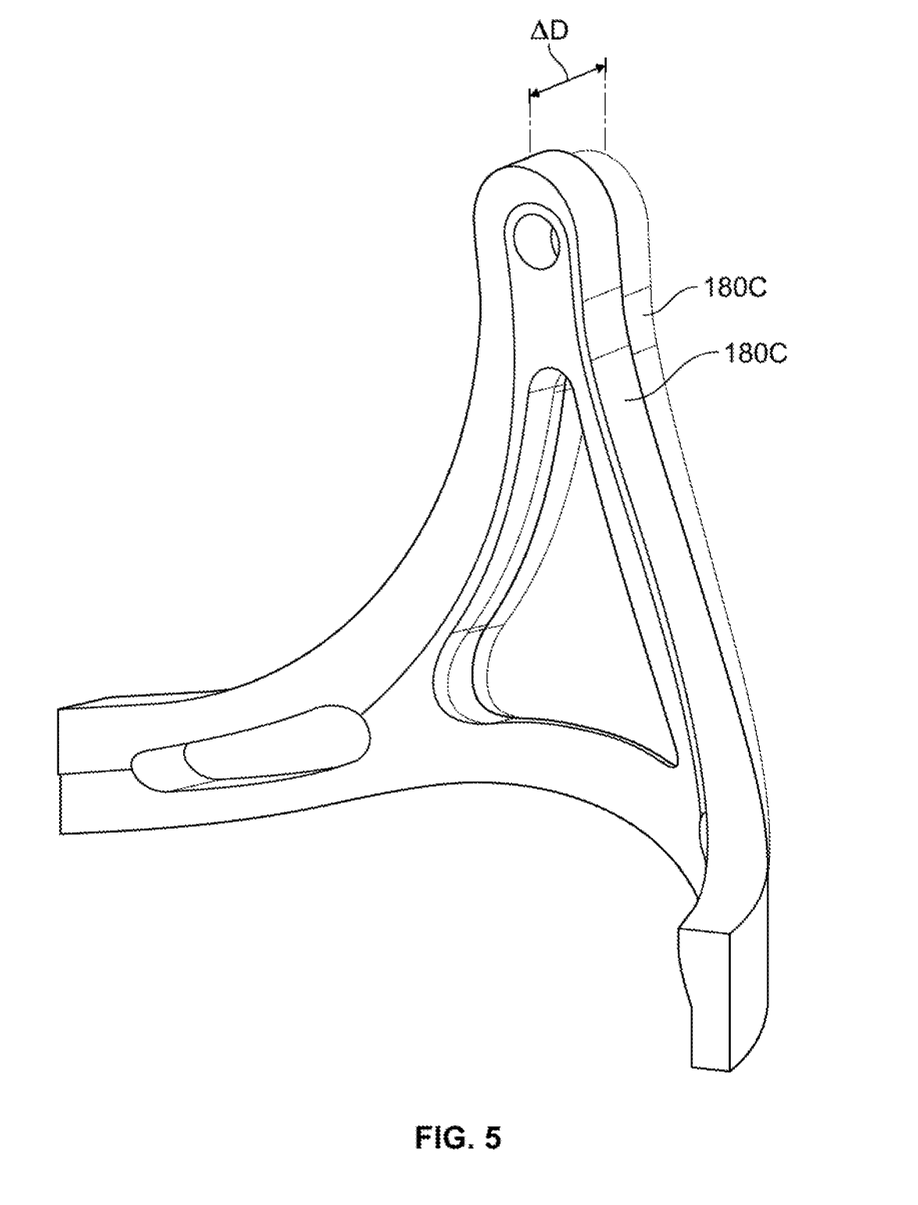
FIG. 5 is a ⅓ side perspective view showing the deflection of the stent post tip upon the application of external forces.

The use of a polymer to form stent 100 allows for greater durability of the stent and prosthetic heart valve during both handling and implantation of the prosthetic valve as compared to prior art stents comprised of metal. In particular, polymers generally have an elastic deformation curve that extends over a large range of stresses, whereas metals may exhibit elastic deformation under low stresses, but may deform plastically under higher stresses. Thus, the use of polymers rather than metals reduces the possibility of plastically deforming the overall diameter or circumference of the stent. Additionally, once the completed valve is surgically implanted within the body, coaptation of the leaflets will cause the post tips to deflect. For example, FIG. 5 illustrates the deflection of post tip 180C inwardly by an amount ΔD. The polymer stents 100 of the present invention minimize the amount of post tip deflection ΔD to no greater than about 3 mm. However, some small amount of deflection may be desirable. Therefore, the amount of post tip deflection is preferably greater than 0 mm and less than 3 mm.

Providing an injection molded monolithic polymeric stent further allows for design modifications to the geometry of the stent that are unavailable or unfeasible when designing metal stents. For example, as previously discussed in the background section, conventional metal stents have an inflow edge region with a width that is substantially similar to the width of the outflow edge region. This uniform design provides for a stable stent structure that allows surgeons to easily grasp the valve assembly with minimal deformations to the stent. However, in contrast, the polymer stents of the present invention have an outflow edge portion 130 with a greater width than the inflow edge portion 128. Despite this difference, deflection of no greater than about 3 mm at the tips of the commissure posts 160 can be achieved. This amount of deflection resembles the strength and minimal degree of deflection of conventional metallic stents.

In order to achieve the same structural and mechanical properties as metallic stents, it is desirable to form polymeric stents with a greater overall thickness. The thickness T of polymeric stents can be substantially greater than the thickness of typical metal stents, lending to greater durability of the stent before and after implantation, while exhibiting at least the same strength and deflection properties as a metal stent. In that regard, polymeric stents according to the present invention may have a thickness T (FIGS. 2-3) from about 0.50 mm to about 1.15 mm, depending on the size of the stent and the polymeric material forming the stent. Furthermore, the thickness may be substantially constant throughout the stent. Alternatively, the thickness may be greater at the outflow edge portion 130 of the stent than at the inflow edge portion 128, such as where it is desirable to minimize the cross-section of the stent confronting blood flow. Moreover, the thickness of the stent may be less along a central longitudinal section of the commissure portions 160 (i.e., in the areas immediately adjacent openings 122 and 132), such as to minimize stress concentrations that could potentially lead to stent failure under stress.

A particularly preferred polymer for forming stent 100 is PolyEtherEtherKetone ("PEEK"). PEEK is a high-performance, semi-crystalline thermoplastic. Its ability to retain mechanical and chemical resistance properties at high temperatures makes it a good candidate for stent 100. The Young's modulus of PEEK is 3.6 GPa and its tensile strength ranges from 90 to 100 Mpa. PEEK has a glass transition temperature at around 143° C. (289° F.) and it melts at around 343° C. (662° F.). It is highly resistant to attack by both organic and aqueous environments. These characteristics of PEEK make it biologically compatible and enable it to be implanted within the human body. Although many grades of PEEK may be employed for forming the stents 100 of the present invention, PEEK-816-00 Victrex® 151G, available from Victrex PLC of Lancashire, United Kingdom, is preferred. In addition to PEEK, stent 100 may be formed from other types of polymers, including without limitation polysulfone (e.g., PES-1024-00 Radel® AG320 NT-760, available from Solvay Specialty Polymers); polyphenylsulfone (e.g., PPSU-2804-00 Radel® R-5800 NT, available from Solvay Specialty Polymers); liquid crystal polymer (e.g., LCP-001 Vectra® A1115 natur, available from Ticona, United States); polyoxymethylene (e.g., POM-1748-00 Hostaform® C27021, available from Ticona, United States); and polypropylene (e.g., PP-1851-00 Bormed™ HD850M0, available from Borealis Nucleation Technology).

Figure 3:
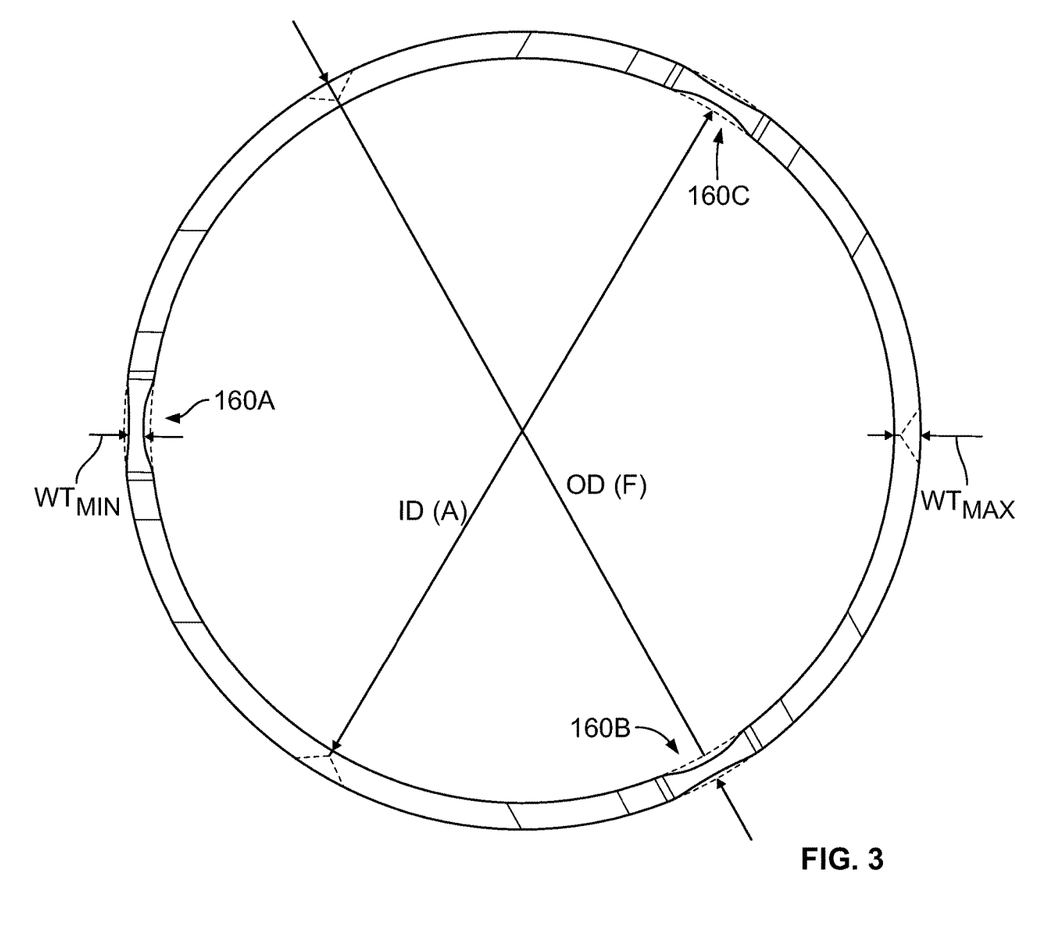
FIG. 3 is a top plan view of the stent in FIG. 2.

The polymeric stent configurations that can be constructed and arranged in accordance with the present embodiments are numerous. Examples of such configurations are provided in Table A below. Dimensions T1-T6, R1-R4, post height ($H_C$), and total stent height ($H_T$) referred to in Table A are shown in FIG. 4; and inner diameter ("ID"), outer diameter ("OD"), minimum wall thickness ("$WT_{MIN}$") and maximum wall thickness ("$WT_{MAX}$") are shown in FIG. 3. The dimensions in Table A are merely exemplary, and various modifications thereof may be made within the scope of the present invention.

TABLE A

| Stent Size mm | T1 mm | T2 mm | T3 mm | T4 mm | T5 mm | T6 mm | R1/R5 mm | R2 mm | R3 Mm | R4 mm | W1 mm | Nom Inner Diam "ID" mm | Wall thickness $WT_{MIN}$-$WT_{MAX}$ mm | Post Hgt $H_c$ mm | Total Hgt $H_T$ mm | Nom Outer Diam "OD" mm |
|---|---|---|---|---|---|---|---|---|---|---|---|---|---|---|---|---|
| 19 | 0.8 | 1 | 0.8 | 1 | 0.6 | 0.9 | 0.73 | 0.472 | 0.365 | 0.55 | 2.4 | 16.821 | 0.65-0.865 | 10.17 | 11.59 | 17.9 |
| 21 | 1 | 1.4 | 0.8 | 1.4 | 0.8 | 0.9 | 0.77 | 0.55 | 0.3 | 0.5 | 2.2 | 18.79 | 0.65-0.87 | 11.88 | 12.7 | 19.88 |
| 23 | 1 | 1.4 | 1 | 1.4 | 0.6 | 1 | 0.77 | 0.54 | 0.45 | 0.5 | 3 | 20.768 | 0.65-0.856 | 11.88 | 13.6 | 21.83 |
| 25 | 1.2 | 1.8 | 1.25 | 1.8 | 0.65 | 1 | 0.95 | 0.61 | 0.44 | 0.5 | 3.5 | 22.928 | 0.65-0.786 | 12.9 | 14.8 | 23.85 |
| 27 | 1.5 | 2 | 1.25 | 2 | 0.7 | 1 | 1.55 | 0.86 | 0.46 | 0.5 | 3.5 | 26.289 | 0.65-1.056 | 14.68 | 16.9 | 27.75 |
| 29 | 1.5 | 2 | 1.25 | 2 | 0.7 | 1 | 1.55 | 0.86 | 0.46 | 0.5 | 3.5 | 26.43 | 0.65-0.985 | 14.68 | 16.9 | 28.645 |

Figure 6:
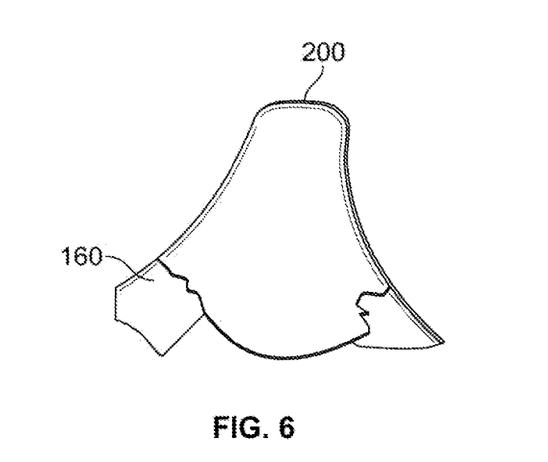
FIG. 6 is a perspective view of a portion of the stent of FIG. 2 with a covering thereover.
Figure 14:
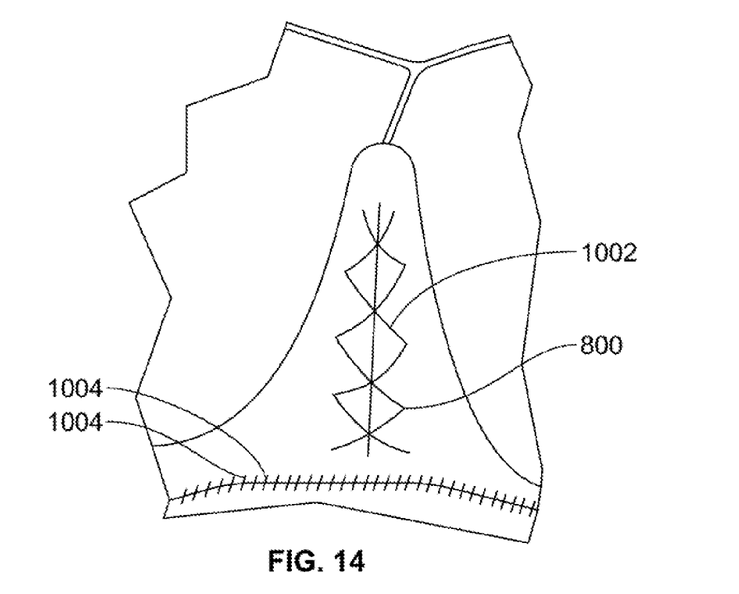
FIG. 14 is an enlarged schematic view of a representative portion of an assembly of components in accordance with the invention.
Figure 15:
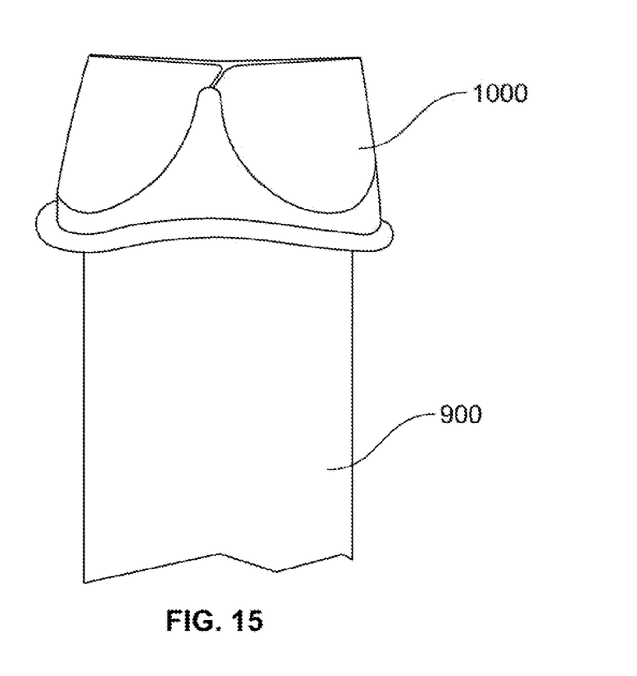
FIG. 15 is a top perspective view of an assembly in accordance with the present invention provided on the tool shown in FIG. 13.
Figure 16:
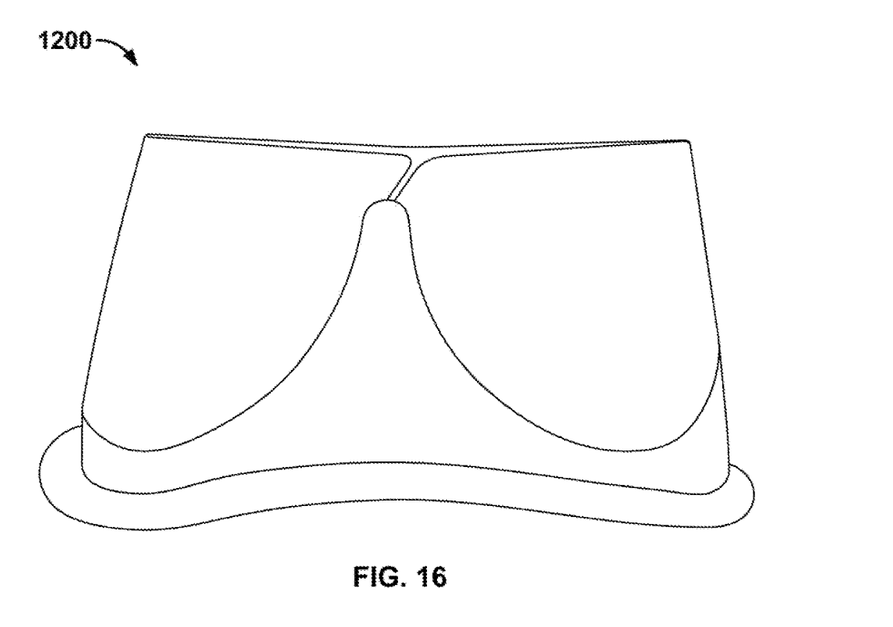
FIG. 16 is a perspective view of a completed prosthetic heart valve in accordance with the invention.

With reference now to FIGS. 6-16, once the size of the prosthetic heart valve to be implanted has been determined and the appropriate size stent 100 has been selected, the fabric and tissue may be assembled onto the stent to provide a completed prosthetic heart valve assembly 1200 (FIG. 16). Turning first to FIG. 6, a sleeve-like fabric cover 200 can be provided over each commissure post 160. As shown, fabric commissure tip cover 200 extends over the apex 181 of the respective commissure post 160. Tip covers 200 help prevent post tips 180 from poking through the additional fabric and tissue that will be mounted on the stent. One example of a suitable fabric for use in making covers 200 is reemay fabric, which is a spun form of polyester, although other types of fabric may be used. Fabric covers 200 can be secured in place by suturing to the associated post tip 180.

Figure 7:
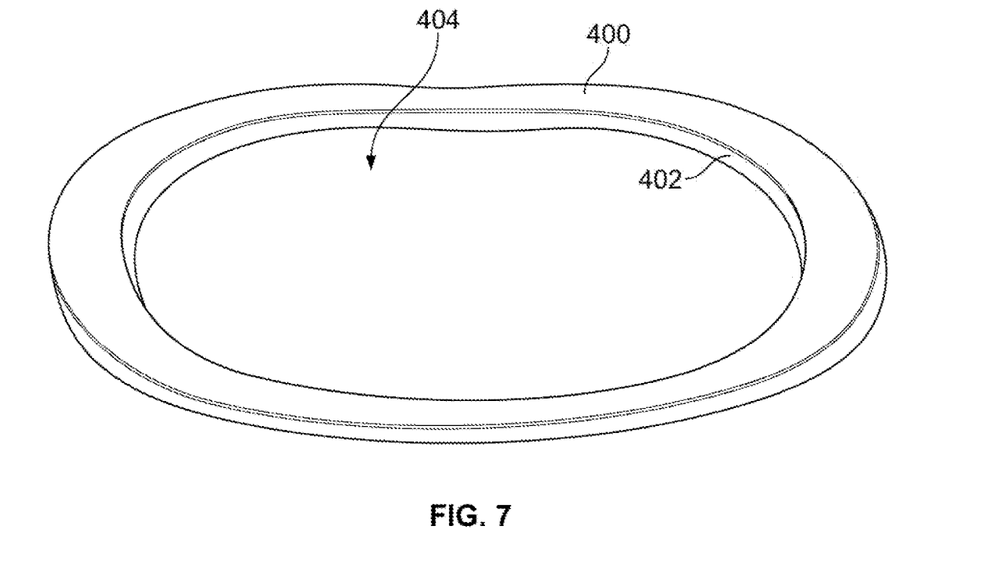
FIG. 7 is a perspective view of another component prior to assembly to the stent shown in FIG. 2.
Figure 8:
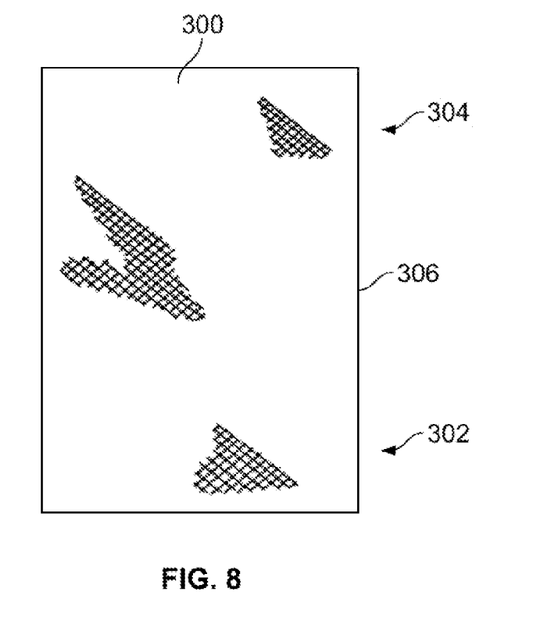
FIG. 8 is an elevational view of another component prior to assembly to the stent shown in FIG. 2.
Figure 9:
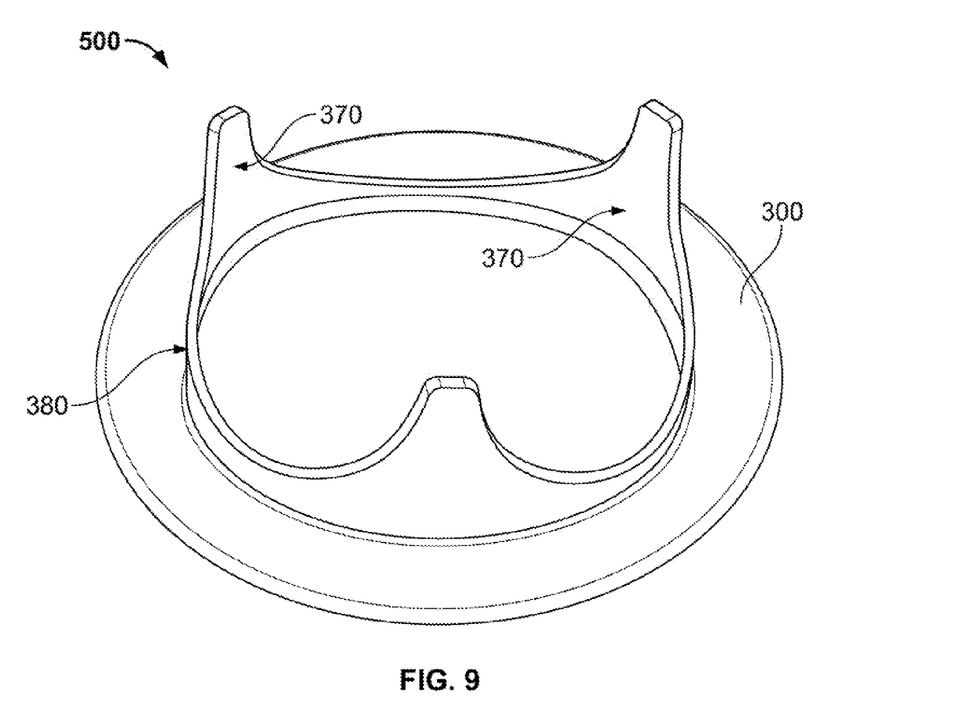
FIG. 9 is a perspective view of an assembly of the components of FIGS. 2 and 6-8 in accordance with the present invention.

An illustrative embodiment of a cuff filler ring 400 is shown in FIG. 7. Ring 400 has an annular shape with scalloped edges extending around an opening 404. FIG. 8 illustrates an embodiment of a polyester fabric tube 300 for use in assembling prosthetic valve 1200. Tube 300 is essentially an elongated piece of fabric in a tubular configuration. Stent 100 (with coverings 200) and ring 400 (FIG. 6) may be placed coaxially around the outside surface 306 of a lower portion 302 of fabric tube 300. Ring 400 may be placed around stent 100 so that the inner edge 402 of the ring is adjacent to and around the inflow edge portion 128 of the stent. In a preferred arrangement, ring 400 will be positioned around stent 100 so that the scalloped edges of the ring are aligned with the scalloped contour of the inflow edge portion 128 of the stent.

With the components properly positioned, the upper portion 304 of tube 300 may be inverted and pulled down over the exposed outer surface of stent 100 and ring 400 and pulled tightly enough to conform to outflow edge portion 130. Sutures may be used to hold all of these components together as an assembly 500 shown in FIG. 9, so that stent 100, fabric covers 200, and ring 400 are completely encased within fabric 300. Upper portion 304 of fabric 300 conforms closely to stent 100 above ring 400, and in particular, follows the scalloped contour of outflow edge portion 130 around the circumference of assembly 500.

Figure 10:
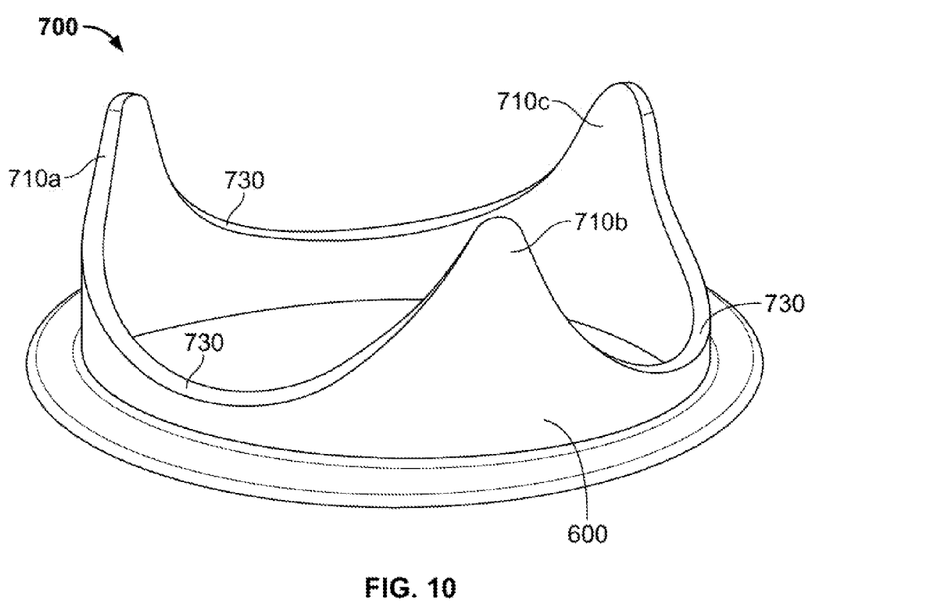
FIGS. 10 and 11, respectively, are perspective top and bottom views of the assembly of FIG. 9 with another component added in accordance with the invention.
Figure 11:
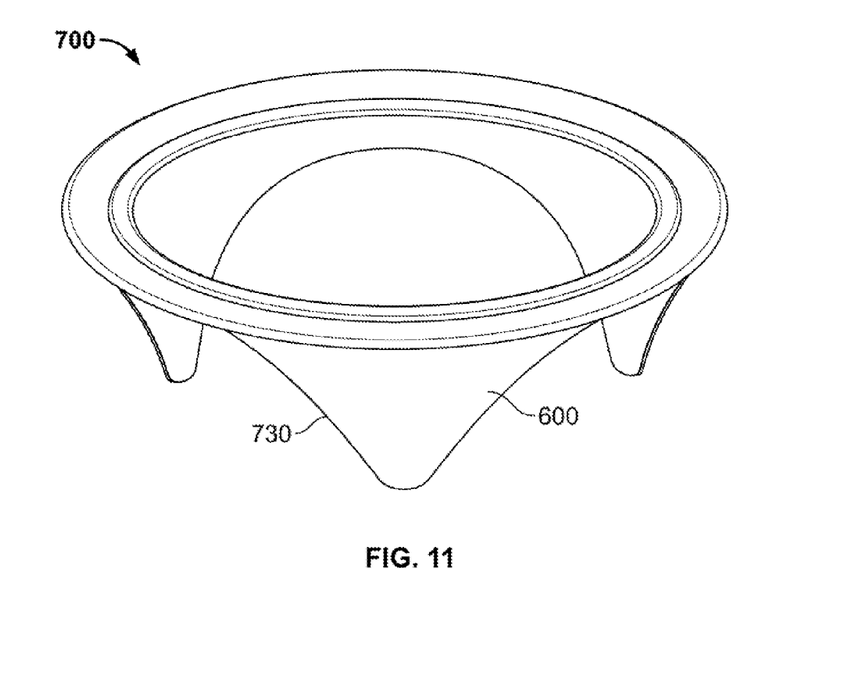

Once the fabric covering 300 is in place, tissue may be mounted onto the assembly 500. Referring to FIG. 10, tissue 600, such as porcine pericardium, may be mounted onto the exposed inner surface 370 and outer surface 380 (FIG. 9) of assembly 500 so that each surface of the assembly is covered in tissue. Sutures may be used to secure tissue 600 to assembly 500. Once completed, the assembly 700 shown in FIGS. 10-11 results. The addition of tissue 600 can help to enhance the durability and reduce the thrombogenicity of the finished valve. Apart from somewhat thickening the overall structure of the predecessor assembly 500, the addition of tissue 600 does not significantly change the shape of any portion of the assembly 700.

Although porcine pericardium is mentioned above for tissue 600, other types of tissue may be used to cover assembly 500 if desired. Examples of such other possible tissue include any mammalian pericardium (e.g., equine or bovine pericardium).

Figure 12:
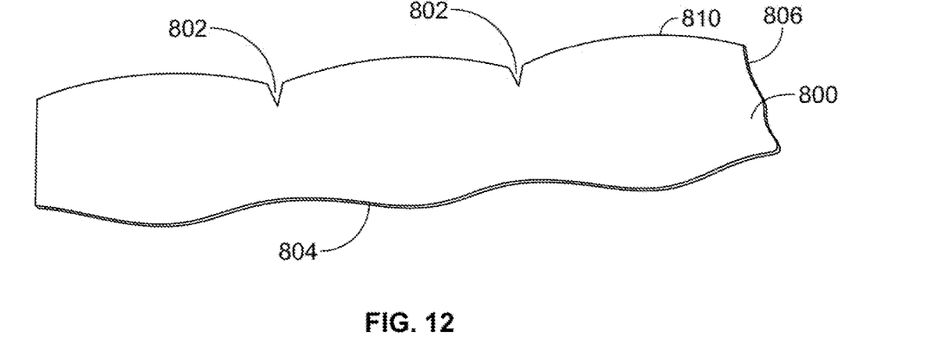
FIG. 12 is a perspective view of tissue prior to assembly with the stent assembly shown in FIG. 9.

With tissue 600 in place, leaflets can be added to the assembly 700 using a pre-formed sheet 800 of tissue, such as a sheet of bovine pericardium tissue. Referring to FIG. 12, sheet 800 has been die cut to a shape that can be used to form all three leaflets of a finished valve. Note that lower edge 804 of sheet 800 (as viewed in FIG. 12) is scalloped to conform to the blood-inflow edge of the stent 100 and the overall scalloped shape of the finished valve assembly 700. Upper portion 806 of sheet 800 forms the three leaflets of the valve. Shallow downward cuts 802 are positioned between the individual leaflet portions adjacent the upper edge 810 of sheet 800, but sheet 800 preferably remains a unitary sheet so that it can be used to form all three leaflets in the finished valve. Although bovine pericardium is mentioned above as the tissue forming sheet 800, it is to be appreciated that other types of tissue may be used in its place. Examples of such other possible tissue for sheet 800 include any mammalian pericardium (e.g., equine or porcine pericardium).

Figure 13:
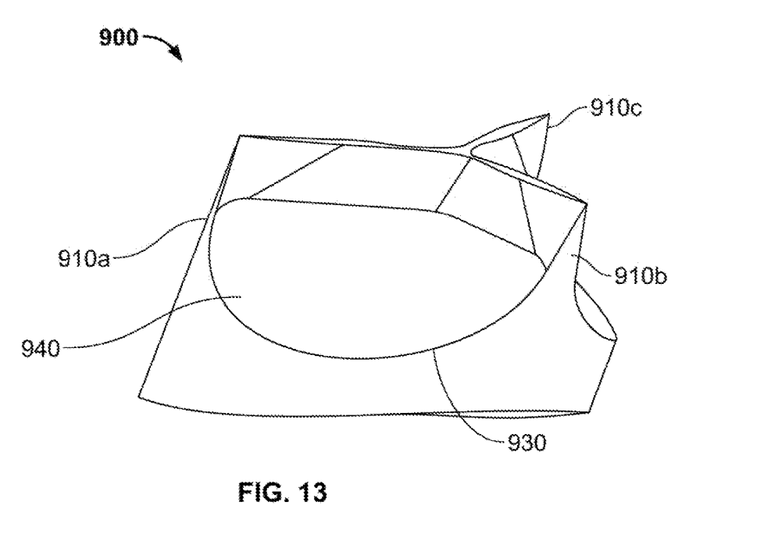
FIG. 13 is a perspective view of a tool that is useful in the manufacture of heart valves in accordance with the invention.

FIG. 13 illustrates a tool 900 that can be used in the manufacture of valve 1200. Tool 900 may be a mounting mandrel that can be inserted coaxially into assembly 700 so that each of the commissure portions 910a-910c of the mandrel is angularly or rotationally aligned with a respective one of the commissure portions 710a-710c (FIG. 10) of assembly 700. In addition, each of the scalloped edge portions 930 of mandrel 900 may be positioned adjacent a corresponding scalloped outflow edge portion 730 of assembly 700.

With mandrel 900 positioned inside of assembly 700, as described in the preceding paragraph, sheet 800 may be wrapped around the outside of assembly 700 above the sewing cuff portion of the assembly. The sewing cuff portion is the portion that includes ring 400 in its interior. This wrapping may be done with the scalloped lower edge 804 of tissue 800 just above and conformed to the scalloped sewing cuff of assembly 700. In addition, each of cuts 802 may be adjacent a respective one of two of commissures 710, and the extreme left and right edges of tissue 800 may come together adjacent the third commissure 710. The portion of tissue 800 above each outflow edge portion 730,930 may then be pressed radially inwardly so that it resets on the adjacent concave surface 940 of mandrel 900. Tissue 800 may be stitched to assembly 700 (but not to mandrel 900) in this condition. For example, FIG. 14 shows stitching 1002 that may be used to hold the initially free, left and right edges of tissue 800 together adjacent one of the commissures 710 of assembly 700. Other stitching 1004 in FIG. 14 is used to stitch tissue 800 to assembly 700 all the way around the assembly just above the sewing ring portion of the assembly. The resulting valve structure shown in FIG. 15 may be referred to as assembly 1000.

FIG. 15 shows assembly 1000 still mounted on mandrel 900 as described in the immediately preceding paragraphs. Note in particular that the portion of tissue 800 above each of outflow edge portions 730 remains pressed in against the adjacent concave surface 940 of mandrel 900. With assembly 1000 in this condition on mandrel 900, the assembly may be subjected to fixation of the tissue. Such fixation of the tissue may be accomplished using any conventional and suitable means, including cross-linking of the tissue by exposing it to cross-linking agents such as glutaraldehyde or epoxides such as TGA (triglycidyl amine). Such fixation of the tissue stabilizes the tissue and renders it substantially biologically inert and bio-compatible. The fixation of the tissue in contact with shaped surfaces 940 also gives the tissue a bias to return to that shape when it is not subjected to external forces. On the other hand, the fixation still leaves the tissue sufficiently flexible that the leaflet portions of tissue 800 above outflow edge portions 730 can deflect outwardly to open the valve and let blood flow out when a ventricular contraction pressurizes the blood in the ventricle below the valve. When that ventricular pressure ceases, however, the leaflet portions above outflow edge portions 730 come together again (coapt) and close the valve.

After the tissue of assembly 1000 has been subjected to fixation as described above, assembly 1000 can be removed from mandrel 900. The result is a completed prosthetic heart valve 1200 as shown in FIG. 16. In use, valve 1200 has the operating characteristics described in the preceding paragraphs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   an annular stent having a base and annularly spaced commissure portions projecting from the base, each commissure portion including a tip, the stent including an inflow edge on the base, an outflow edge extending between the tips, and a plurality of openings between the inflow edge and the outflow edge, each of the openings having a first edge extending generally parallel to the inflow edge at a first spaced distance from the inflow edge and a second edge extending generally parallel to the outflow edge at a second spaced distance from the outflow edge, the second spaced distance being greater than the first spaced distance, and the stent being comprised of a polymeric material;
   a fabric covering the stent;
   a first layer of tissue covering the fabric; and
   a second layer of tissue overlying the first layer of tissue and including leaflet portions that extend inwardly between annularly adjacent ones of the commissure portions.

2. The prosthetic heart valve according to claim 1, wherein the polymeric material is polyetheretherketone.

3. The prosthetic heart valve according to claim 1, wherein the polymeric material is selected from the group consisting of polysulfone, polyphenylsulfone, liquid crystal polymer, polyoxymethylene, and polypropylene.

4. The prosthetic heart valve according to claim 1, wherein the stent has a wall thickness between about 0.50 mm and about 1.15 mm.

5. The prosthetic heart valve according to claim 1, wherein at least one of the tips has a tip deflection less than about 3 mm when the heart valve is in use in a patient.

6. The prosthetic heart valve according to claim 1, wherein at least one of the tips has a tip deflection greater than about 0 mm and less than about 3 mm when the heart valve is in use in a patient.

7. The prosthetic heart valve according to claim 1, wherein the first spaced distance is between about 0.4 mm and about 1.2 mm.

8. The prosthetic heart valve according to claim 1, wherein the second spaced distance is between about 0.6 mm and about 2.2 mm.

9. The prosthetic heart valve according to claim 1, wherein the stent has a first wall thickness at the inflow edge and a second wall thickness at at least a portion of the outflow edge, the second wall thickness being greater than the first wall thickness.

10. The prosthetic heart valve according to claim 1, wherein the second layer of tissue comprises bovine pericardium tissue.

11. The prosthetic heart valve according to claim 1, further comprising a sewing cuff structure adjacent the base of the stent.

12. The prosthetic heart valve of claim 1, wherein the first edge generally follows the contour of inflow edge and the second edge generally follows the contour of outflow edge.

* * * * *